_US005104661A_

United States Patent [19]

Lau

[11] Patent Number: 5,104,661
[45] Date of Patent: Apr. 14, 1992

[54] REVERSE LOADING OF LIPOSOMES

[75] Inventor: John R. Lau, Wooster, Ohio

[73] Assignee: Technology Unlimited, Inc., Wooster, Ohio

[21] Appl. No.: 648,315

[22] Filed: Jan. 29, 1991

Related U.S. Application Data

[63] Continuation of Ser. No. 393,298, Aug. 14, 1989, abandoned.

[51] Int. Cl.$^5$ ............................................. A61K 37/22
[52] U.S. Cl. ..................... 424/450; 424/1.1; 428/402.2; 264/4.1; 264/4.3; 264/4.6
[58] Field of Search .................. 424/450, 1.1; 264/4.3, 264/4.1, 4.6; 428/402.2

[56] References Cited

U.S. PATENT DOCUMENTS

| | | | |
|---|---|---|---|
| 4,448,765 | 5/1984 | Ash et al. | 424/450 |
| 4,483,929 | 11/1984 | Szoka | 435/7 |
| 4,603,044 | 7/1986 | Geho et al. | 514/3 |
| 4,708,861 | 11/1987 | Popescu et al. | 424/1.1 |
| 4,839,175 | 6/1989 | Guo et al. | 424/450 |
| 4,880,635 | 11/1989 | Janoff et al. | 424/450 |
| 4,885,172 | 12/1989 | Bally et al. | 424/450 X |
| 4,946,683 | 8/1980 | Forssen | 428/402.2 X |

*Primary Examiner*—Thurman K. Page
*Assistant Examiner*—Donald R. McPhail
*Attorney, Agent, or Firm*—Frijouf, Rust & Pyle

[57] ABSTRACT

The first part explains the discovery, and means to employ the discovery that whole, intact vesicles and liposomes are not the sole means of burden (drug) delivery by targeting molecules. The second part teaches the discovery of reverse loading of vesicles and liposomes to obtain fully functional core volume load of a useful burden without the trauma degradation of the active burden material, and with greatly extended shelf life.

3 Claims, No Drawings

REVERSE LOADING OF LIPOSOMES

This is a Continuation of application Ser. No. 07/393,298, filed Aug. 14, 1989, now abandoned.

FIELD OF THE INVENTION

Lipid membrane structures coupled with pharmacologically active burden.

DESCRIPTION OF THE PRIOR ART

At the time of the discovery that is this invention, the development of liposomal systems is well advanced. The literature provides specific instructions for making vesicles and liposomes by sonication, microfluidization, detergent dialysis and other techniques utilizing the phenomena of cavitation. One may refer to prior U.S. Pat. No. 4,603,044 for instruction both in making vesicles and supplying target molecules for directing the vesicle to the hepatocyte.

Applicant, as well as all known researchers heretofore, have endeavored to capture a core volume of the drug or other material during the formation of the vesicle. As a film of lipid material is sonicated, for example, most of it will form the vesicle configuration with bipolar walls and capture some of the media, in which it is formed, within the core volume.

Some have recognized that there are other means of associating the drug with the liposomal system. See publication "Uptake of Antineoplastic Agents into Large Unilamellar Vesicles in Response to a Membrane Potential" by Lawrence D. Mayer, Marcel B. Bally, Michael J. Hope and Pieter R. Cullis, published in 1985. Elsevier Science Publishers.

The above-referenced publication must be carefully categorized, because the teaching of the publication is considerably apart from the novelty of the present invention.

The publication stresses potassium ion diffusion potential to achieve effective interior concentrations. The publication assumes, as Applicant and all other researchers prior to this time have assumed, that the formation of vesicles produces a bladder configuration having an internal core volume. It is the placing of drugs or diagnostic material into that core volume that has been the prior art endeavor.

In this document, a generic term "burden" will be used to refer to the many substances that have been captured in vesicles of bipolar lipids. See "Definitions" below. This document will show a novel concept of diffusion loading and partitioning, which will include bipolar lipids.

Furthermore, the method of filling vesicles by formation in a water solution of the desired drug or diagnostic material has been expensive because the trauma of microfluidization, and other procedures causes a considerable degradation of the burden. Insulin is an outstanding example. Formation of vesicles heretofore in a bath of insulin solution has resulted in polymerization of considerable amounts of the insulin rendering the insulin molecules antigenic. Although the bath of insulin can be reused to form more loaded liposomes, each reuse produces a greater concentration of polymerized molecules and a lower grade of product. Insulin is exceedingly expensive and degradation of the bath causes a considerable cost factor in conventional manufacture of drug filled vesicles.

DEFINITIONS

Pharmacologically active burden: As used herein, is a drug, diagnostic substance, physical enhancement substance such as a skin moisturizer, perfume, dental plaque counter agent or fluoride, but not limited thereto. The invention is in the means and method of loading liposomes or fragments without limit to the particular substance constituting the burden.

Bipolar device: a liposome, and fragment particles of a lipid membrane structure.

Liposome and vesicle: Both bladder forms having bipolar walls. There is no clear consensus for selection of one term or the other, and therefor are considered interchangable in this specification.

SUMMARY OF THE INVENTION

This invention resides primarily in the discovery that a bipolar lipid, either in a bladder form or in fragments, will not only load a drug or diagnostic material by diffusion, such as in the case of a fully formed vesicle, but by partitioning in both types of structures.

Partitioning is the phenomena that exhibits some type of solubility of materials in a media which normally are considered to be insoluble in that media. For example, oil and water are said not to mix and generally this is true. Nevertheless, a mixture of the two, when separated, will exhibit a small amount of oil in the water and a small amount of water in the oil. This is known as partitioning.

With the discovery that partitioning is taking place both in fully developed vesicles and bipolar lipid fragments, it is then the discovery of this invention to join a targeting molecule and a drug or other burden together by means of a lipid intermediary.

It is, further, an object of the invention to load the core volume of vesicles, and to partition drug or diagnostic material to the walls thereof and to lipid fragments, both inside the membrane and outside the membrane.

It is the principal object of this invention to construct a fully operative targeted carrier for a drug or other burden without degrading trauma formerly associated with energy loading of vesicles and liposomes during formation in the presence of the burden.

Vesicles and liposomes are made in several different ways known to the art. (Gregory Gregoriadis, *Liposomes Technology* Vol. I, II, III, CRC Press, 1984). By whatever means employed, the general principal is that a lipid is mixed with water or a water-based solution, and energy is applied to cause the lipid to form into the bladder configuration. The formation process captures some of the water medium within the core volume.

GENERAL DISCLOSURE

Applicant distinguishes over all known prior art, including intensive literature studies, by the discovery that: a) vesicles can be manufactured in a buffer solution with none of the desired burden present, and thereafter supplied with the burden by means of diffusion and/or partitioning.

Study of the effort to diffuse insulin into a buffer solution in the core of vesicles disclosed that faulty vesicles, fragments of vesicles, and similar lipid particles, not only carry the desired drug or diagnostic material, but also took on a target molecule and acted in the same manner as fully developed vesicles and liposomes. No diffusion potential has been found to be necessary for producing fully effective targeted liposome structures either as vesicles or discontinuous lipids.

DESCRIPTION OF THE PREFERRED EMBODIMENT

In the discussion that follows, the term dispersed phase will refer to those substances (i.e. generally lipids) that are dispersed throughout the dispersion medium. In other words, the dispersed phase is the discontinuous phase, whereas the dispersion medium is regarded and defined as the phase that is continuous. Buffer or water are examples of the continuous phase.

As a result of the invention, we have been able to target vesicles and liposomes to selected sites of action in vivo to elicit specific pharmacological responses. These targeted delivery systems are working examples of utilizing a structured and dispersed lipid phase that resides in a continuous aqueous medium to achieve beneficial results. This invention will extend the concept of targeted drug delivery to include those species in the dispersed phase of a continuous medium that have structures different from the classical liposomes and vesicles and yet still are capable of evoking the desired pharmacological response.

This invention employs dispersed phases to selectively sequester, entrap, embed, absorb or adsorb specific targeting molecules, such as biliverdin, monoclonal antibodies or diphosphonates, as well as molecules designed to inhibit reticuloendothelial (RES) uptake of the dispersed phase drug delivery system. The invention includes the entrapment, embedding or adsorption of drugs, vitamins, diagnostics, or combinations thereof, for the purpose of creating an efficacious drug delivery system. As a result, a dispersed phase delivery system is created in the dispersion medium which can be visualized and function as an isolated platform to which target, RES avoidance and drug molecules can be associated or attached.

The fact that the dispersed phase is lipid-like and may be composed of a variety of lipid molecules points to the versatility of lipid compositions that may be selected for dispersed phase applications.

Thus, it is now recognized according to this invention, that a compartmentalized core volume, such as encountered in vesicles or liposomes, is not necessarily a prerequisite for effective drug delivery. Instead, these new forms of dispersed phase drug delivery platforms rely on the phenomena of adsorption, partitioning, or on specific means of covalent or non-covalent attachment of molecules to achieve the desired objective. It is stressed that target molecules, RES avoidance molecules or biological actives such as drugs, diagnostics, hormones, vitamins, pesticides, plant nutrients or growth factors, enzyme inhibitors or activators, DNA and RNA gene fragments, therapeutics in general, anticancer agents, bone active agents, sunscreen, insect repellants and perfumes, and the like, are examples which we now associate effectively with targeted lipids.

Since dispersed phases have a large surface area due to their colloidal nature, numerous sites exist for surface adsorption and partitioning phenomena to occur. Likewise, dispersed phases offer sites where the partitioning of molecules may commence. A molecule is said to partition when it has preference for one phase over the other. Generally molecules partition more readily into phases that exhibit the same solubility properties as the molecules themselves. Thus partitioning is a matter of degree. Molecules that are similar in solubility properties are said to exhibit a high partitioning coefficient.

Throughout this specification the formation of the vesicles and their post formation loading according to this invention will be discussed with respect to insulin. It must, however, be clearly understood that any burden material that is capable of being captured by the vesicle will benefit by the teaching of this invention.

When a solution of insulin is employed as the medium in which the vesicles are formed, the high energy input of the vesicle formation procedure will subject the insulin to possible dimerization and polymerization reactions. If polymeric forms of insulin result, they will depart significantly from the desired, simple monocomponent entity. These polymeric forms of insulin can elicit immunogenic problems. Immunogenic considerations play an increasingly significant role as chronic dosing of a given drug is pursued.

In the practice prior to this invention, in order to form vesicles by microfluidization, sonication or other known processes, large volumes and concentrations of insulin are required. As an example, 1.48% W/V concentration of lipid microfluidized with the insulin concentration at 131.7 units/ml costs on the order of $5,000 U.S. or more per liter of solution. When the insulin which is not associated with the vesicle is removed, close to 99% of that insulin is either wasted or slated for recovery by recycle. Both processes are costly, not only in terms of raw material, but also in manufacturing time for personnel and equipment.

According to this invention, empty or blank vesicles are formed in an idealized sterile buffer solution. By empty it is meant that the sterile buffer solution is not the ultimate desired cargo for the vesicle. The vesicles are not literally empty; they are devoid of the intended cargo or burden and filled with the buffer. The buffer of choice has been 40.5 mM $NaH_2PO_4$—NaOH pH 7.3.

In the vesicle making procedure, after vesicles are manufactured or synthesized in sterile media or buffer, they may then be stored in this state for longer periods of time because there is an absence of either biologically or chemically active molecules which could interact or otherwise disrupt the vesicle. Therefore, storage of empty, but membrane permeable, vesicles is greatly facilitated and advantageous.

The invention is simplicity in its essence. A vesicle or permeable lipid membrane is formed in an environment of a sterile medium and having the core volume filled with that medium. The improvement of this invention comprises loading the core volume by immersing the prior formed vesicle in solution of the desired substance compatible with the core volume media. That is, the vesicles, which are said to be empty in respect to their content of the drug or diagnostic material, are filled through the naturally occurring physical phenomenon, thereby leading to a simple compartmentalization of insulin.

Prior art publication "*Uptake of Antineoplastic Agents into Large Unilamellar Vesicles in Response to a Membrane Potential*" supra, obtains core volume content by creating a $K+$ potential. In contrast the present invention is the discovery of the roll of post formation loading by diffusion without the need of first creating a potential.

If pores exist in a vesicle, then vesicle pores may be sealed up with an annealing process that is conducted at a temperature above the transition temperature of the membrane lipids. It is not necessary to seal the pores.

When appropriate targeting molecules are introduced into the vesicle membrane, the vesicle can then be targeted to the intended site of action. In the example set forth below, hepatobiliary molecules on the surface of the vesicles are used to target the vesicle to the liver hepatocyte. In this particular example, the vesicle core volume contains insulin.

In order to test this invention, experiments have been completed which establish that the aforementioned procedure has great utility and efficacy in delivering insulin for the treatment of the diabetic state in a rat having the diabetic state induced by streptozotocin. Efficacy with the animal model relates to the significant decrease in peripheral blood or plasma glucose levels two hours post-dosing when compared to the controls with native insulin only.

A clear advantage is achieved in relation to the amount of native insulin used in synthesizing the hepatocyte directed vesicle insulin drug product. In this procedure, porous vesicles, which are said to be blank or empty, are incubated for a period of time of at least 20 minutes with the appropriate dosing solution and then injected into the animal. Note that the usual dose is employed. By incubating as described, some of the dose will be a burden of lipid targeted to the liver, and the remainder will be free to serve the peripheral system.

The vesicles used in the experiment were made by the principals of this invention simply by utilizing the process of diffusion and partitioning to encapsulate or compartmentalize anywhere from less than 1% to a few percent of the total insulin in solution. The encapsulated insulin is targeted by an hepatobiliary target molecule to the liver hepatocyte in order to achieve the desired pharmacological effect. See U.S. Pat. No. 4,603,044 for one example of targeting procedures. Thus, the need to synthesize vesicles by microfluidization or other means of vesicle formation, which requires large volumes and concentrations of insulin, is eliminated.

METHOD OF MANUFACTURE

In order to maximally incorporate core volume insulin, the solubilized external insulin needs to approach saturation levels. However, it is not necessary or even required, to load the core volume of the vesicle with insulin or any other biologically active drug, diagnostic material, molecule, or nutrient to the level or saturation. This specification teaching only illustrates that it is a practical procedure to load vesicles to a utility level in this fashion.

1) Preparation Procedure

The following lipids illustrated in Table I were mixed together and solubilized in $CHCl_3.MeOH$ (2:1 w/v) and dried down under vacuum before being hydrated in pyrogen-free distilled deionized water.

TABLE I

| Category | DPL | CHOL | DCP | MPB-PE | Proto-IX Dimethyl Ester | Total |
|---|---|---|---|---|---|---|
| MW | 733 | 387 | 546 | 980 | 591 | |
| Mg | 505.05 | 48.72 | 162.41 | 67.40 | 7.22 | 790.80 |
| u moles | 689.02 | 125.89 | 297.45 | 68.78 | 12.22 | 1193.36 |
| mole ratio | 5.47 | 1 | 2.36 | 0.546 | 0.097 | |
| mole % | 57.74 | 10.55 | 24.93 | 5.76 | 1.02 | 100% |
| % by wt | 63.87 | 6.16 | 20.53 | 8.53 | 0.91 | 100% |

790.80 mg of lipid/72 ml of lipid Stock A = 10.98 mg/ml
790.80 mg of lipid/516 ml total volume = 1.53 mg of lipid/ml or 0.153% w/v The 790.80 mg of lipid was hydrated in 72.0 ml of PF ($DeH_2O$) at 42° for 20 minutes by slow turning on the Buchi rotoevaporator. The hydrated lipid was then diluted to 516 ml total volume with enough 0.2 M $NaH_2PO_4$—NaOH pH 7.3 such that the final concentration was 40.5 mM. The 516 ml of suspended lipid was allowed to stir for 15 minutes at ambient temperature before being processed in the microfluidizer at 50 p.s.i.g. head pressure resulting in 12,000 p.s.i.g. shear pressure. Following microfluidization the sample was centrifuged in the Sorvall RC-2B refrigerated centrifuge at 20,000 rpm (49,460×g) at 15° for 30 minutes. A small dilution was made in the preparation at this point, resulting in a final buffer concentration of 39.8 mM. The sample was filtered through a 0.2 u Acrocap filter and stored in the refrigerator under $N_2$ at 4° C.

2) Post-formation Loading Procedure

The post-formation loading procedure was performed by mixing 1.0 ml of vesicles in 39.8 mM $NaH_2PO_4$—NaOH pH 7.3 buffer with 1.0 ml of insulin stock solution prepared at a concentration of 0.874 mM in 15.1 mM $NaH_2PO_4$—NaOH pH 7.3 buffer. The mixing resulted in a suspension where the final concentration of insulin was 0.437 mM, and a final buffer concentration of 27.45 mM $NaH_2PO_4$—NaOH pH 7.3. The loading procedure was allowed to proceed for 18 hours at 4° C.

Following the incubation in the refrigerator at 4° for 18 hours, the vesicles were annealed at 45° C. for 20 minutes with slow turning on the Buchi rotoevaporator. The closing of the vesicle pores commences as annealing begins. The degree of leaking is a matter of operator choice, controlling the variables of time, temperature, and buffer, as known in the art.

The great advantage of vesicle loading by the above disclosure, is that no separation of filled vesicles from the media insulin is required. When a dose of insulin is required, the shelf supply of blank vesicles is mixed with the prescribed dose, and the mix used as an injection. All of the insulin is used. There is no degraded product. The success of this procedure is founded on the discovery that no specific portion of the insulin need be targeted to the liver. The liver, it has been found, will respond to any portion of the dose reaching the liver via the loaded vesicles. The free or native insulin is then used by the peripheral organs.

Having completely proven the discovery that formed vesicles with neutral core volume could be reverse loaded by diffusion, the evidence of laboratory work indicated that targeted units were reaching the hepatocyte even though there were few if any vesicles formed.

Accordingly, a run of vesicles was made by the classical sonication method and then the vesicles were separated from the solution by chromatography.

After this separation process, which is known to be very efficient and therefor could be expected to remove substantially all of the vesicle forms, the remaining dispersed phase showed examples of targetable membrane fragments, lipid particles and fragments each with a burden component and a targeting molecule.

When tested, these fragments and similar items performed as vesicles have in the past. Accordingly, the test thus conducted has proven the theory of partitioning to apply to these fragments and to thereby act as fully developed drug delivery systems.

Also, this experiment has conclusively shown that very small quantities of insulin partitioned into the lipid fragments has thereby been found to be sufficient to program the liver for proper glucose uptake and distribution.

In review, this disclosure recognizes that prior methods of vesicle loading generally results in degrading of the active burden as well as producing a defective vesicle wall structure through the introduction of active burden into the lipid domain.

The disclosure then compares the greatly reduced defect factor in vesicles formed in water or buffer with no active ingredient present with prior art.

Also, with no active ingredient present, shelf-life of blank vesicles is greatly extended.

Finally, the disclosure teaches incubating the blank vesicles in a physiologically active solution. Whether the result is diffusion, partitioning or some unknown attraction of active material and lipid forms, it is a fact that the new method of loading produces a result of far greater effectiveness, and great cost reduction.

Although vesicles of greater integrity result from formation in inactive media, the best loading requires purposely formed pores in the membrane wall. Diffusion loading can occur in perfectly formed vesicle walls, but deliberate pore formation allows greater and faster diffusion.

What is claimed is:

1. The method of supplying a burden of a physiologically active ingredient to a bipolar device, comprising the steps of:

(1) mixing a water or buffer solution of the burden material in a concentration from zero to a first degree such that the solution is effectively physiologically inactive, and applying energy to the mixture sufficient to cause formation of liposomes with a burden of said water solution, and:

(2) thereafter soaking the resultant of step (1) with a physiologically active ingredient of a concentration higher than that in said liposomes, whereby loading of the burden into the liposomes is achieved due to a higher concentration of the active burden ingredient in the exterior aqueous compartment.

2. The method of claim 1 wherein the combination of soaked liposome and active ingredient is processed to separate the liposomes from the external remaining active ingredient.

3. The method of filling the core volume of liposomes, comprising:

incorporating a lipid mix into an aqueous medium, said lipid mix being of a formulation that will provide for a porous wall liposome;

forming liposomes from said mix by energy imput, whereby a core volume of said aqueous medium is captured in the formed liposomes; and thereafter soaking said liposomes in a drug or diagnostic solution of higher solute content than said aqueous medium, thereafter closing the pores by annealing.

* * * * *